United States Patent

Bokros et al.

Patent Number: 5,376,111
Date of Patent: Dec. 27, 1994

[54] HEART VALVE PROSTHESES

[75] Inventors: Jack C. Bokros; Michael R. Emken, both of Austin; Axel D. Haubold, Liberty Hill; T. Scott Peters, Georgetown; Jonathan C. Stupka, Austin, all of Tex.

[73] Assignee: ONX, Inc., Austin, Tex.

[21] Appl. No.: 919,284

[22] Filed: Jul. 24, 1992

[51] Int. Cl.$^5$ ............................................. A61F 2/24
[52] U.S. Cl. ............................................. 623/2
[58] Field of Search ............... 623/2; 137/512.1, 527

[56] References Cited

U.S. PATENT DOCUMENTS

| | | | |
|---|---|---|---|
| 3,546,711 | 12/1970 | Bokros | 3/1 |
| 4,078,268 | 3/1978 | Possis | 3/1.5 |
| 4,272,854 | 6/1981 | Bokros | 3/1.5 |
| 4,274,437 | 6/1981 | Watts | 137/527 |
| 4,308,624 | 1/1982 | Klawitter | 3/1.5 |
| 4,328,592 | 5/1982 | Klawitter | 3/1.5 |
| 4,363,142 | 12/1982 | Meyer | 3/1.5 |
| 4,373,216 | 2/1983 | Klawitter | 3/1.5 |
| 4,443,894 | 4/1984 | Klawitter | 3/1.5 |
| 4,451,937 | 6/1984 | Klawitter | 3/1.5 |
| 4,692,165 | 9/1987 | Bokros | 623/2 |
| 4,808,180 | 2/1989 | Johnson | 623/2 |
| 4,863,458 | 9/1989 | Bokros | 623/2 |
| 4,888,010 | 12/1989 | Bokros | 623/2 |
| 5,026,391 | 6/1991 | McQueen et al. | 623/2 |
| 5,080,669 | 1/1992 | Tascon et al. | 623/2 |
| 5,116,366 | 5/1992 | Hwang | 623/2 |
| 5,116,367 | 5/1992 | Hwang et al. | 623/2 |
| 5,123,920 | 6/1992 | Bokros | 623/2 |
| 5,137,532 | 8/1992 | Bokros et al. | 623/2 |
| 5,147,390 | 9/1992 | Campbell | 623/2 |
| 5,152,785 | 10/1992 | Bokros et al. | 623/2 |
| 5,192,309 | 3/1993 | Stupka et al. | 623/2 |

FOREIGN PATENT DOCUMENTS

| | | |
|---|---|---|
| 8902254 | 3/1989 | WIPO |
| 9221305 | 12/1992 | WIPO |

Primary Examiner—Randall L. Green
Assistant Examiner—Elizabeth M. Burke
Attorney, Agent, or Firm—Fitch, Even, Tabin & Flannery

[57] ABSTRACT

Mechanical heart valve prostheses having either a single occluder or a pair of occluders are designed to permit such occluders to assume an open position parallel to the longitudinal axis of the valve passageway. The pivot arrangements are such that an occluder pivots about a constant center or pivot axis substantially offset from the locations where engagement occurs between the occluder and the valve body, whereby prompt smooth pivoting movement toward the closed position is initiated from an open position parallel to the valve centerline. For example, elongated arcuate shoes protruding from lateral edges of the occluders follow arcuate paths of matching complementary curvature defined by grooves in diametrically opposed flat sidewall sections of the valve body.

21 Claims, 3 Drawing Sheets

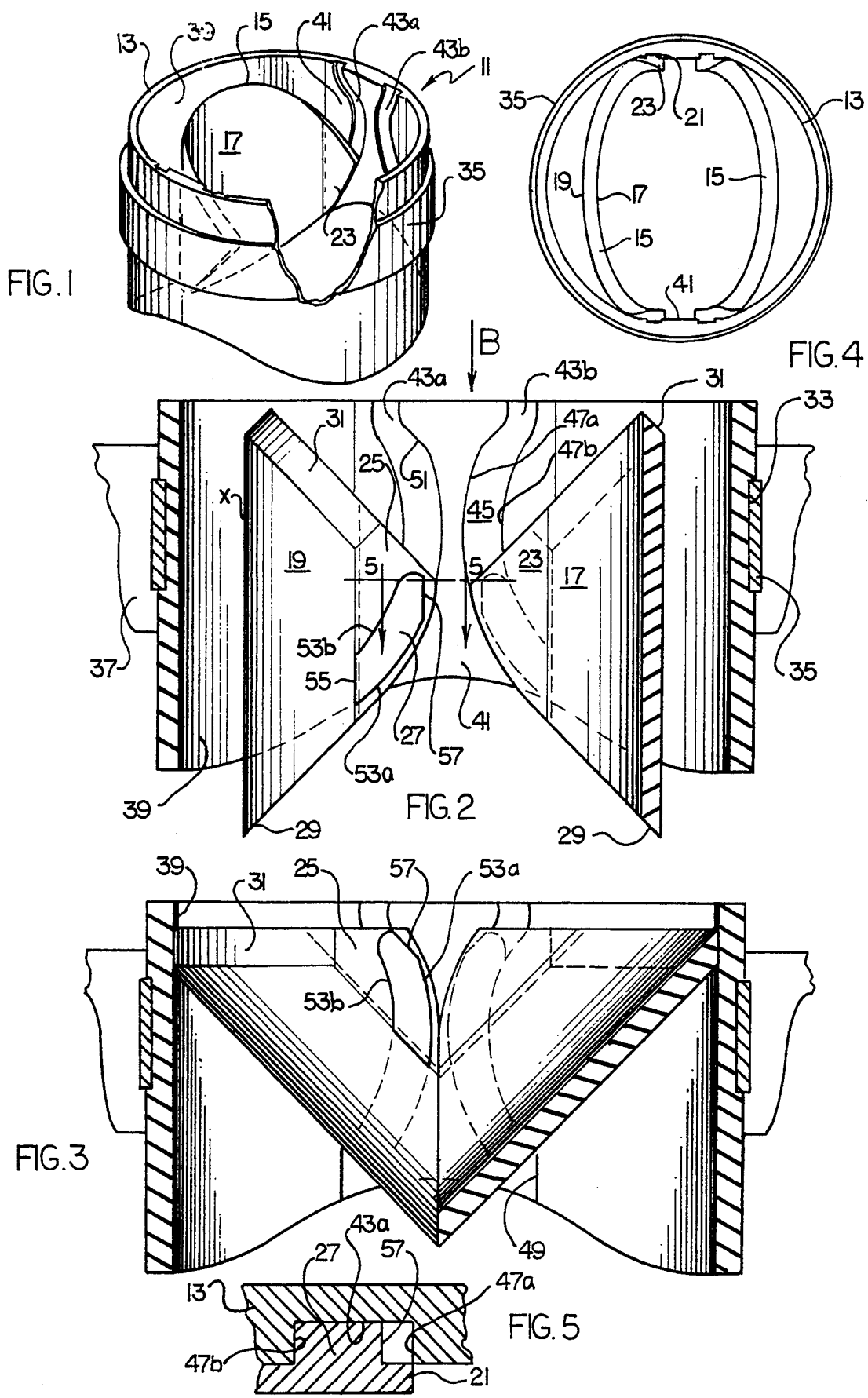

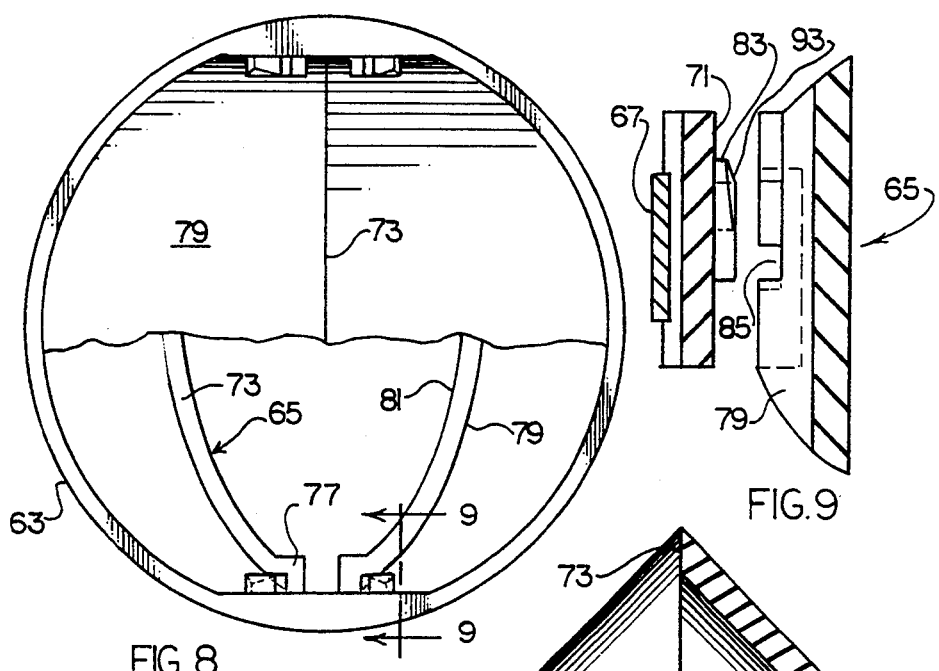
FIG. 8
FIG. 9
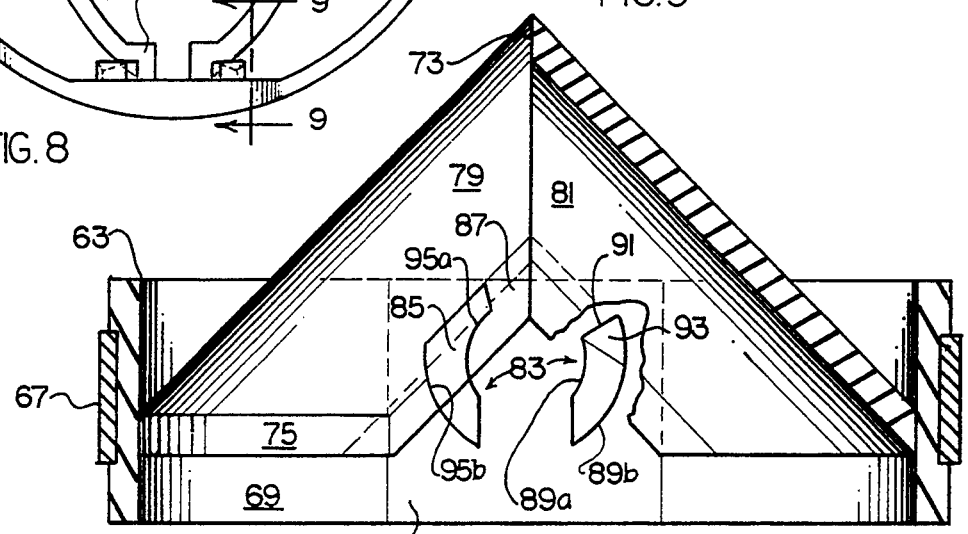
FIG. 7
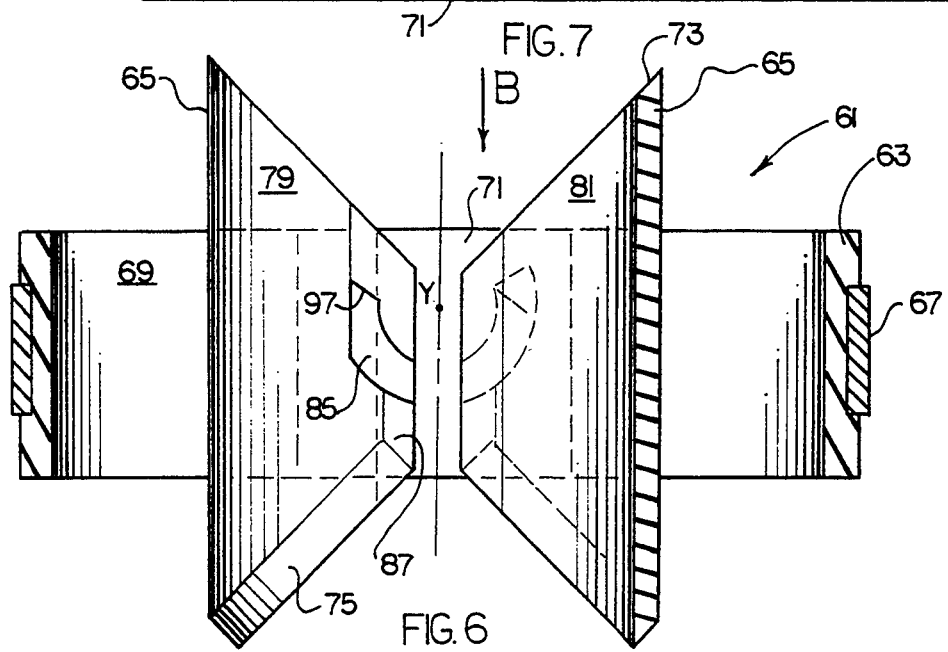
FIG. 6

HEART VALVE PROSTHESES

FIELD OF THE INVENTION

The present invention relates to mechanical heart valve prostheses and, in particular, to improved prosthetic heart valves having valve members or occluders which open to provide very low resistance to flow therethrough but which reliably pivot to promptly move from the open to the closed position.

BACKGROUND OF THE INVENTION

A wide variety of heart valve prostheses have been developed to operate hemodynamically, in conjunction with the pumping action of the heart, to take the place of defective natural valves. These valves variously have valve bodies which are designed to function either with a single occluder or a pair of occluders or leaflets, which occluders generally pivot along eccentric axes (or both pivot and translate) to open and close a central blood flow passageway through the valve body.

U.S. Pat. No. 3,546,711 (Dec. 15, 1970) shows a single occluder valve wherein a circular disc pivots about a fixed axis which is offset, in the downstream direction, from the plane of the occluder in the open position.

U.S. Pat. No. 4,373,216 (Feb. 15, 1983) discloses both single occluder and bi-leaflet heart valves wherein protrusions extend generally radially inward from a pair of flat sidewall sections of the valve body. Valve members, which have slots in their lateral edges to receive such protrusions, are guided in generally pivoting about an axis adjacent the upstream edge thereof and translating to reach their closed position.

U.S. Pat. No. 4,308,624 (Jan. 5, 1982) discloses heart valves of both the single occluder and bi-leaflet type having curved valve members which both rotate and translate in moving between the open and closed positions. Although the leaflets were intended to be able to assume a parallel orientation in the open position, as shown in FIG. 3, study of the valve arrangement shows that, upon reversal of blood flow through the passageway, although pivoting could occur in the intended manner, the leaflets could also translate upstream without beginning to rotate toward the closed position. Once the leaflets have so moved upstream (having been guided by the paths the spherical ears trace in the slots 21), one or both of the leaflets might possibly counterrotate because of the instantaneous attitude of bloodstream flow and, as a result, not close on that stroke. U.S. Pat. Nos. 4,328,592 and 4,443,894 (Apr. 24, 1984) disclose later versions of this valve; both illustrate embodiments wherein the leaflets in their open position are angled relative to the centerline plane (see Column 4, lines 39–43 of the U.S. Pat. No. '894 patent). Thus, when flow reversal occurs (as depicted in FIG. 4), because of the alignment of angled surfaces 44 of the stops 41 and the placement of the stops, potential inward pivoting or counterrotation of the leaflets is precluded (see Column 5, lines 34–41).

U.S. Pat. No. 4,363,142 (Dec. 14, 1982) discloses a bi-leaflet heart valve wherein the leaflets have laterally extending ears in the form of generally oval or spherical projections that are received in recesses of complementary design.

U.S. Pat. No. 4,451,937 (Jun. 5, 1984) shows additional single occluder and bi-leaflet valves wherein valve members pivot and translate to their closed positions, being guided, in part, by laterally extending ears 21 which move in generally arcuate slots or depressions 23. The valve members are of necessity oriented at an angle to the centerline plane in the open position.

U.S. Pat. No. 4,692,165 (Sep. 8, 1987) discloses single occluder and bi-leaflet valves wherein valve members have notches in their lateral edges which receive arcuate posts protruding from flat sidewall sections of the valve body; the posts and associated stops guide the pivotal and translational movement of the valve members.

U.S. Pat. No. 4,863,458 (Sep. 5, 1989) discloses bi-leaflet heart valves having leaflets of varying thickness which are guided in generally pivotal movement by laterally extending ears 54 that are sectors of a sphere and are received in modified, generally spherical recesses 48 formed in the flat sidewall sections of the valve bodies. The ears each have a flat, inboard surface 53 but otherwise have a spherical surface 55 (see FIGS. 5 and 9). The flat surface 55 engages the flat stop surface 97 in the full open position wherein the leaflets are oriented at a substantial angle to the centerline (see FIG. 2) so that the backflow of blood will cause prompt pivoting to the closed position.

U.S. Pat. No. 4,808,180 (Feb. 28, 1989) discloses a bi-leaflet valve wherein the leaflets each have a semi-conical shape and thus inherently provide significant resistance to blood flow through the valve in the open position. The leaflets are guided by generally C-shaped rails (FIG. 3) that protrude from the valve body sidewall and that are received in recesses of complementary shape in the lateral edges of the semi-conical leaflets (FIG. 5).

Commercially developed heart valves, using valve members of the type generally exemplified by various of the above-mentioned U.S. patents, have always employed those valve members oriented at an angle to the centerline plane in the open position so that, when backflow of blood begins, it preferentially impinges upon the outflow surfaces of each valve member and thus initially imparts a pivotal component to its closing movement. It is now felt to be particularly important that a mechanical heart valve prosthesis should provide a passageway through which blood can flow freely in the open position with a minimum of drag. To accomplish this desired objective, it is now believed that the valve members should be able to assume a low-energy orientation which is usually parallel to the longitudinal axis of the passageway; however, in such orientation, the valve members must still be highly responsive to backflow so as to close quickly with a minimum of regurgitation. Improvements in valve construction have continued to be sought with the objective of creating mechanical valves having such characteristics.

SUMMARY OF THE INVENTION

The present invention provides mechanical heart valve prostheses having the aforementioned desirable characteristics wherein a valve member or members can assume an open position parallel to the longitudinal axis of the valve passageway, but it will promptly and reliably begin to pivot toward the closed position orientation as soon as backflow past such valve member occurs within the valve. These valves include a pivot arrangement wherein interengaging elements are located at two diametrically opposed flat sidewall sections of the valve body and at corresponding lateral locations on each valve member. For example, shoes or ears having pairs of inboard and outboard arcuate surfaces may protrude from opposite lateral surfaces of each valve member, proportioned so as to be slidably received in elongated, arcuate recesses or grooves in the valve body sidewall sections, or the reversal of such parts may alternatively be employed. The recesses are so positioned that, when backflow of blood creates drag forces upon the surfaces of the valve members in a direction tending to displace the valve members upstream, engagement of the appropriate arcuate surfaces of the shoes against the arcuate sidewalls of the recesses is such that each valve member quickly and reliably begins to smoothly pivot toward its closed position orientation.

This arrangement assures that a valve member, even when it is in an open position oriented precisely parallel to the valve centerline at the instant of the beginning of backflow, will promptly begin to pivot or swing toward its closed position orientation, thus assuring reliable, efficient, positive closing action. This desirable closing action is enhanced by shaping and positioning the recesses so that the center of rotation of pivot (CRP) or pivot axis remains constant. For bi-leaflet valve members which close "naturally" (i.e. wherein the downstream edges abut each other in the closed position), the CRP is located a distance from the centerline of the valve body equal to at least about 50% of the radius of the valve passageway and preferably tangent or nearly tangent to the outflow surface. For bi-leaflet valve members which close "unnaturally" (i.e. wherein the upstream edges abut each other in the closed position), the CRP should be at or near to the centerline.

Reliable closing movement is accomplished without the need for any additional interengaging elements on the valve body or on the valve members, and a particularly clean construction can be provided at the interior surface of the valve body wherein the interior sidewall of the valve body can be a purely cylindrical surface except for the two flat, diametrically opposed wall sections. This construction is further enhanced when the valve members are made so that their major exterior surfaces that are exposed to blood flow are essentially totally rectilinear, and by using arcuate shoes which are received in arcuate recesses in the valve body sidewall where they will be out of the major path of the flowing bloodstream. The orientations and shapes of these valve pivot mechanisms preferably have arcuate contact surfaces of generally complementary curvature which extend over substantial lengths so as to assure smooth, nonbinding, sliding movement, and the arrangement is preferably also such as to have the load on the valve members at the instant of closing distributed such as to assure a tight seal is achieved between abutting, mating edge surfaces of two leaflets.

A particular advantage of the single occluder version of the valve is that, in the open position, the passageway can be divided into two nearly equal halves.

BRIEF DESCRIPTION OF THE DRAWINGS

FIG. 1 is a perspective view of a bi-leaflet heart valve embodying various features of the present invention wherein the valve body is shown with only one of the two occluders installed;

FIG. 2 is a cross-sectional view, enlarged in size, of the heart valve of FIG. 1 with both occluders installed and shown in the open position, but with the left-hand occluder shown in elevation, and with the sewing ring installed;

FIG. 3 is a cross-sectional view, similar to FIG. 2, of the heart valve of FIG. 1 shown with both occluders in the closed position but with the left-hand occluder again shown in elevation;

FIG. 4 is a plan view of the heart valve of FIG. 2 with the occluders in the open position;

FIG. 5 is an enlarged fragmentary, sectional view taken generally along the line 5—5 of FIG. 2;

FIG. 6 is a view similar to FIG. 2 showing an alternative embodiment of a hi-leaflet heart valve embodying various features of the present invention designed to open and close "unnaturally", with the occluders shown in the open position and with the left-hand occluder shown in elevation;

FIG. 7 is a view similar to FIG. 6 showing the occluders after they have reached the closed position, with a portion of the right-hand occluder broken away to show the pivot construction;

FIG. 8 is a plan view of the heart valve of FIGS. 6 and 7, with the occluders being shown in the open position in the lower half of the figure and in the closed position in the upper half;

FIG. 9 is an enlarged fragmentary sectional view taken generally along the line 9—9 of FIG. 8 but exploded to show the two elements side-by-side rather than engaged;

DETAILED DESCRIPTION OF THE PREFERRED EMBODIMENTS

Figure 10:
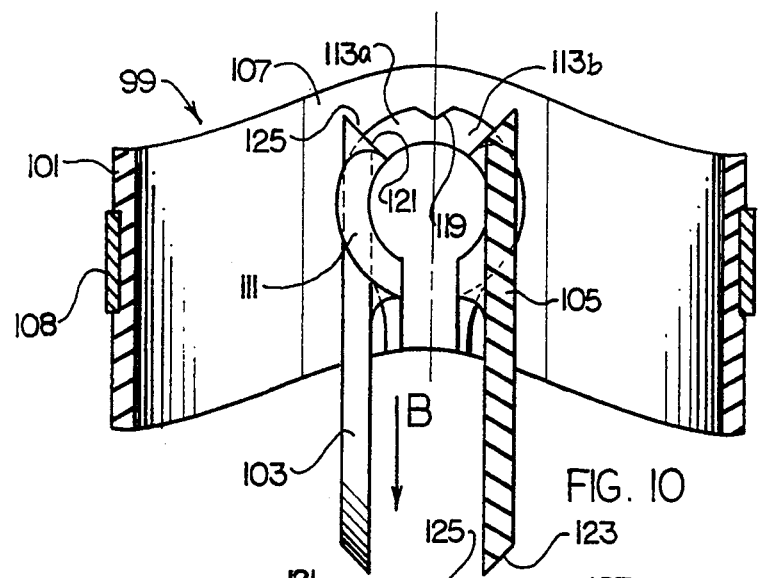
FIG. 10 is a view similar to FIG. 2 of yet another bi-leaflet heart valve embodying various features of the invention wherein flat plates constitute the major portions of the occluders, with the occluders being shown in the open position and the left-hand occluder being shown in elevation.

Depicted in FIGS. 1 through 5 is a bi-leaflet heart valve 11 which incorporates a valve body 13 and a pair of curved leaflets 15, although for clarity of illustration, only one of the two leaflets is shown in FIG. 1. Each of the pair of leaflets 15 has a concave inflow surface 17 and a convex outflow surface 19, both of which surfaces are rectilinear, i.e. being defined by a plurality of straight lines. These rectilinear surfaces form the main body portion of the leaflet which generally has a wall of uniform thickness. Each leaflet includes a pair of side sections 21 which have generally flat interior and exterior surfaces 23, 25. An arcuate ear 27 protrudes laterally from each exterior flat surface 25 and interengages with the valve body to define the pivoting movement of the leaflets. In essence, therefore, each leaflet 15 is generally a section of a tube or hollow cylinder of elliptical or oval cross section, except for the substantially flat side sections 21, as perhaps best seen in FIG. 4. Moreover, each leaflet 15 has a flat downstream mating edge 29 and an upstream arcuate edge 31. The pivot arrangement allows the leaflets 15 to assume an orientation in the open position with their rectilinear surfaces parallel to the centerline of the valve body and thus substantially parallel to the flow of blood through the valve. As a result of its construction, as best seen in FIGS. 2 and 4, the valve 11 has an enlarged central flow channel in its open position compared to valves of this general type employing flat leaflets as, for example, the one illustrated and described hereinafter.

The valve body 13 is relatively elongated in its axial length, having a minimum axial dimension equal to about ½ of the diameter of the valve body passageway and being scalloped to provide a pair of tapered skirt sections. These sections extend, in a downstream direction, another 35 to 45% of the minimum axial dimension, measured to the very bottoms of the skirts, at two diametrically opposed locations. The valve body 13 is generally annular in shape, being essentially cut from a hollow right circular cylinder having a groove 33 in its exterior surface designed to accommodate a metal stiffening ring 35. The stiffening ring 35 provides rigidity to the relatively thin valve body which may be made of pyrolytic carbon or pyrolytic carbon-coated graphite, and the stiffening ring is used to facilitate the attachment of a standard sewing ring 37, as well known in the valve art which facilitates the suturing of the valve in place in the human heart. An otherwise cylindrical interior sidewall surface 39 of the valve body 13 is interrupted by a pair of diametrically opposed flat wall sections 41; however, all the interior surfaces of the valve body are smooth and parallel to the centerline of the passageway. The proportioning of the leaflets 15 is such that the exterior surfaces 25 of the flat side sections 21 of the leaflets are located in essentially sliding contact with the flat interior wall sections 41 of the valve body, thus providing both bearing surfaces and seals in these regions. In the closed position as seen in FIG. 3, the arcuate upstream edge 31 of each leaflet seals against the interior cylindrical surface 39 of the valve body.

To define the movement of the leaflets within the valve body, a pair of arcuate grooves 43a and 43b, which are mirror images of each other, are provided in each flat sidewall section 41 of the valve body. The grooves 43 are preferably open at their upstream and their downstream ends to provide for cleansing flow of blood therethrough, and each contains a central arcuate working section 45 defined by a pair of inboard and outboard (with respect to the centerline plane) sidewalls 47a,b of constant and generally complementary curvature. By centerline plane is meant a plane containing the centerline of the valve passageway of generally circular cross section which plane is perpendicular to the pair of diametrically opposed, parallel flat sidewall sections 41. By complementary curvature is meant that the pair of walls of each groove are spaced apart from each other a distance that is substantially constant for the length of the section in question, e.g. being arcs of concentric circles. Each of the grooves has a flat wall 49 which serves as a downstream stop and a flat wall section 51 which serves as an upstream stop. The downstream and upstream stops lie adjacent to the downstream and upstream ends of the central arcuate working sections of the grooves 43.

The ears 27 of the leaflets are proportioned to be slidingly received in the grooves 43 and translate therein from the downstream end of the working section 45 to the upstream end thereof. As best seen perhaps in FIG. 2, the ears 27 are elongated in shape having arcuate walls 53a and 53b which are of complementary constant curvature, e.g. being arcs of concentric circles. The length of each arcuate ear is preferably at least about twice the width of the ear, and its dimensions and the curvature are such so that the ear will be slidingly received within the groove and will be able to translate upstream and downstream smoothly and without binding. Each of the ears 27 is provided with a flat downstream wall surface 55 and a flat upstream wall surface 57, which walls, as best seen in FIG. 2, are parallel to each other; they are also substantially parallel to the centerline of the valve when the leaflets are in the open position. The width of each arcuate ear 27 is slightly less than the width of the arcuate working section 45 of the groove to assure that there will be smooth movement of the ear within the grooves with no binding.

As well known in this art, the leaflets 15 are installed in the valve body by squeezing the valve body at diametrically opposed locations so as to cause the flat wall sections 41 to separate further from each other, thereby allowing the leaflets to be fitted into the passageway of the valve body in their operative positions with the arcuate ears 27 received within the arcuate working sections 45 of the grooves. When the squeezing force is removed, the valve body 13 returns to its original circular configuration, leaving the desired minimal clearance so that the leaflets are pivotally mounted for travel between their closed and open positions. The metal stiffening ring 35 can be appropriately installed, as by shrink-fitting, following the installation of the leaflets, as is usually the case. However, in some instances, it may be preferred to first install the metal ring to improve the structural properties of a pyrocarbon valve body before installing the leaflets.

In the open position illustrated in FIG. 2, normal blood flow through the valve in the downstream direction is indicted by the arrow B, and the leaflets 15 are located with their ears at the downstream ends of the grooves 43. Although the leaflets are curved in profile, their main body surfaces are rectilinear, i.e. made up of a locus of straight lines, and because these rectilinear surfaces are aligned parallel to the centerline of the valve in the open position, the leaflets provide minimal resistance to blood flow in the downstream direction. This desired position is obtained by the appropriate location of the downstream flat stop 49 at the downstream end of each of the grooves 43, which stop is engaged by the flat downstream wall 55 of the ear to thus halt the downward pivoting motion of the leaflet 15 with the rectilinear surfaces in the desired parallel orientation. However, because of the unique construction of the pivot arrangement, as soon as blood flow reverses, frictional drag on the rectilinear surfaces of the leaflets creates forces tending to move the leaflets in the upstream direction, causing the arcuate ears 27 to be thrust generally tangentially to the matching outboard sidewalls 47b of the arcuate groove sections 45, as a result of which the leaflets immediately begin to pivot toward their closed position orientation from such precisely parallel, open position.

The construction is such that there is a prompt and rapid rotation of the leaflets 15 about a center of rotation of pivot (CRP) that is defined by the curvature of the complementary arcuate sidewalls of the working section 45 of the groove. In FIG. 2, the CRP is marked by the point X and is spaced from the centerline plane a distance greater than ½ the radius. Moreover, the CRP is spaced so that the pivot axis is tangent to the outflow surface 19, which is preferred. If not tangent, it is preferably near a point of tangency, and by near is meant within a distance of about five or preferably three percent of the radius. As a result of the position of the CRP, the drag forces effectively drive the leaflet in its closing rotational movement, assuring a prompt response and rapid pivoting of the leaflets to the closed position, and thereby minimizing regurgitation of blood.

The curvature of the outboard sidewalls 47b of the slots is matched to that of the outboard arcuate walls 53b of the ears 27 by being equal or a few percent less than its radius of curvature, and the radius of curvature of the inboard sidewalls 47a of the grooves is the same or within a few percent of that of the inboard walls 53a of the arcuate ears. As a result, smooth sliding movement of the ears within the grooves is assured, and any potential binding is positively prevented. The rotation or pivoting of the leaflets is rapid and continues until the arcuate upstream edges 31 contact the interior cylindrical surface 39 of the valve body. In most instances, it is expected that the leaflets will simultaneously reach this orientation and that the downstream flat edges 29 of the two leaflets will also abut each other as shown in FIG. 3. However, should one of the leaflets reach the closed position just slightly prior to the other leaflet, the flat upstream wall surface 51 of the groove serves as a stop against the flat wall 57 of the arcuate ear to prevent over-rotation. The slight tolerance which is provided between the relative widths of the arcuate ears and the arcuate working section of the grooves is such to allow a slight backing-off, if necessary, once the other leaflet abuts along the mating edges 29.

Thus, in the closed position depicted in FIG. 3, a seal is created along the centerline plane by the abutting mating edges 29. There is also a seal along the interior periphery of the valve body where the upstream arcuate edges 31 abut against the interior cylindrical surface 39 of the valve body and, as previously indicated, by the close tolerances between the flat exterior surfaces 25 of the side sections of the leaflets and the flat wall sections 41 of the valve body. Some slight tolerance is also provided between the lateral surface of the arcuate ear 27 and the base surface of the grooves, as exaggerated in FIG. 5, and when the blood pressure is its highest at the instant of closing, there can be a brief spurt of blood through this region which assures cleansing action and keeps this region free from potential clotting. Moreover, because both the upstream and the downstream ends of the grooves 43 are open, flow of blood therethrough flushes these regions and provides added protection against potential clot formation.

When normal blood flow resumes, the force of the bloodstream against the concave inflow surface 17 of each leaflet causes it to be promptly displaced downward, and this downward displacement is in the form of rotational movement about the CRP defined by the arcuate working sections 45 of the grooves. This pivoting or rotation continues until the flat end walls 55 of the ears contact the stop surfaces 49 at the downstream ends of the grooves. When such contact occurs, the alignment of rectilinear surfaces of each leaflet body is precisely parallel to the centerline, as shown in FIG. 2.

Illustrated in FIGS. 6 through 9 is an alternative embodiment of a heart valve 61 also incorporating various features of the invention. The heart valve 61 has a valve body 63 and a pair of leaflets 65. The valve body 63 has a similar exterior groove which accommodates a metal stiffening ring 67, and it has a cylindrical interior surface 69 except for a pair of diametrically opposed flat sections 71. Whereas, in the valve 11, the leaflets 15 were mounted so as to open and close "naturally" with their downstream mating edges abutting each other in the closed position, the valve 61 is designed and constructed so that the leaflets 65 open and close "unnaturally". More specifically, the leaflets 65 are formed with upstream mating edges 73 and with downstream arcuate edges 75. Each leaflet has a main body portion in the form of a tubular wall of substantially uniform thickness that is flanked by side sections 77 which have a thickness about twice the thickness of the main body, for a purpose to be explained hereinafter. Moreover, because of the "unnatural" closing movement, the leaflets assume a closed position (depicted in FIG. 7) wherein their upstream edges abut each other, and they have convex inflow surfaces 79 and concave outflow surfaces 81.

A similar pivot arrangement to that illustrated with respect to the valve 11 is used except that essentially a reversal of parts is employed. Instead of having grooves in the flat sidewall section 71, a pair of arcuate rails 83 protrude outward from the otherwise flat wall sections. To coact with the rails 83, complementary notches 85 are provided in the side sections 77 of each leaflet; the notches extend radially inward from a pair of lateral, flat, exterior surfaces 87, which in the assembled embodiment generally bear against the flat sidewalls section 71 of the valve body. The rails 83 are provided with inboard and outboard arcuate surfaces 89a, 89b of complementary curvature and with flat upstream end walls 91. Moreover, the upstream lateral surfaces of the rails 83 are preferably chamfered to create oblique surfaces 93. The notches 85 are formed with inboard arcuate sidewalls 95a and outboard arcuate sidewalls 95b of complementary curvature, and the notches are also provided with flat stop walls 97 at the upstream end thereof. The relative proportioning of the rails 83 and the notches 85 is similar to that hereinbefore discussed with respect to the ears 27 and the grooves 43. The curvatures of the inboard walls 89a and inboard sidewalls 95a are similarly matched, as are the outboard counterparts thereof.

The leaflets are installed as earlier indicated by squeezing the valve body 83 to allow the leaflets to be inserted between the diametrically opposed flat sidewall sections 71 with the rails 83 being received within the notches 85. In the open position as depicted in FIG. 6, the leaflets are located as far downstream as they can move and are oriented with the rectilinear inflow and outflow surfaces parallel to the centerline. They are positioned in this orientation by the interengagement of the upstream flat end walls 91 of the rails, which serve as stops, against the flat wall sections 97 of the notches 85. In this position, blood is flowing downstream in accordance with the arrow B in FIG. 6, and the leaflets again provide minimal resistance to blood flow because of the parallel alignment.

As soon as the blood flow reverses, the frictional drag against the rectilinear surfaces of the generally tubular leaflets 65 creates forces that tend to thrust the leaflets in an upstream direction. The arcuate interengaging surfaces of matching curvature of the rails 83 and the notches 85 translates this upstream thrust into a torque upon the leaflet which causes pivoting movement of each leaflet about a CRP, that is defined by the location and orientation of the arcuate rails 83. Preferably the CRP is located at or near the centerline plane, i.e. within a distance therefrom of not greater than 3% of the radius of the valve body passageway. In the illustrated embodiment, the fixed axes about which the two leaflets 65 pivot are colinear, with the CRP being located at the point Y in FIG. 6, exactly on the centerline plane. Having the CRP located on the centerline plane and substantially offset from the location of sliding contact between the rails and the notches assures positive and rapid closing movement with minimum regurgitation. As can be seen from FIGS. 6 and 8, the drag forces against the leaflet inflow and outflow surfaces 79, 81 are the greatest in the regions spaced from the centerline plane, and by locating the CRP on the centerline plane, spaced from the outboard surface 89b of the rail a distance equal to at least about 25% of the passageway radius, a relatively large moment arm is created with respect to these forces, which promotes initial prompt closing movement and continued rapid movement to the closed position.

In the closed position, the upstream mating edges 73 abut each other and the downstream arcuate edge surfaces 75 seat against the cylindrical surfaces 69 of the valve body. As depicted in FIG. 7, the downstream end portions of the rails 83 extend below the notches 85 in an amount equal to about ⅓ of their length. Again, in this position, the tolerances between the rails 83 and the notches 85 allows slight cleansing leakage of blood therethrough to positively guard against clotting, and the provision of the chamfer 93 promotes this controlled cleansing leakage flow. As soon as downstream flow of blood again resumes, the force of the blood against the convex inflow surfaces 79 causes the leaflets to pivot toward the open position, and they quickly reach the orientation shown in FIG. 6 wherein they provide minimal resistance to blood flow and a relatively large center channel for flow in the downstream direction.

Figure 11:
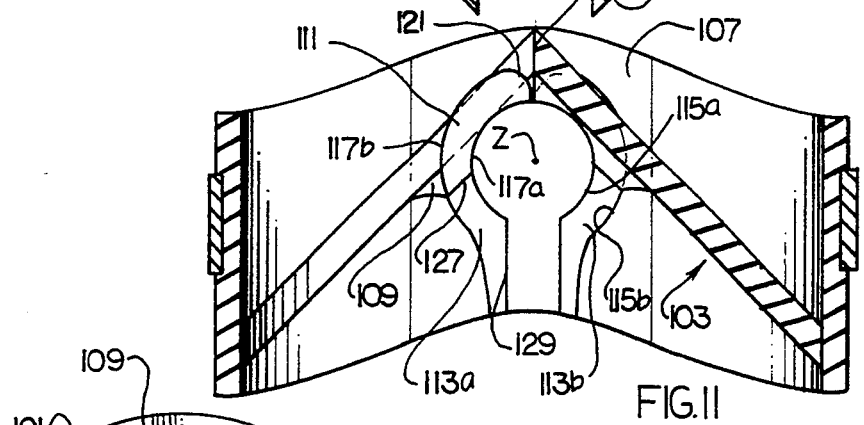
FIG. 11 is a similar sectional view of the valve shown in FIG. 10, but showing the occluders in the closed position.
Figure 12:
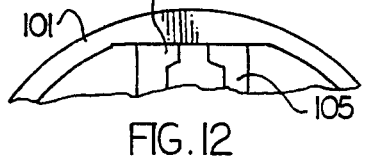
FIG. 12 is a fragmentary top view of the valve of FIG. 10.

Illustrated in FIGS. 10, 11 and 12 is an alternative embodiment of a heart valve 99 which utilizes a valve body 101 and a pair of leaflets 103 which also close unnaturally as in the heart valve 61, but wherein the leaflets have flat main body portions 105. In this embodiment, the valve body 101 is scalloped both top and bottom so as to have a substantially uniform height or axial length about its entire 360° periphery. More specifically, as best seen in FIG. 10, the valve body includes an upstream extension in each region of the usual pair of flat sidewall sections 107, and it has complementarily shaped downstream depressions or cutouts in the two downstream regions in this location. Again, the annular valve body 101 has a shape which is essentially that of a hollow right circular cylinder having a groove in its exterior surface which accommodates a metal stiffening ring 108. The leaflets 103 are flat and of substantially uniform thickness except for side sections 109 of greater thickness from which arcuate ears 111 protrude, as generally in the case of the heart valve 11. The ears 111 are received in a pair of grooves 113a, 113b provided in each flat sidewall section 107 of the valve body, which grooves are mirror images of each other. The grooves 113 are open at their downstream ends and, as best seen in FIG. 10, interconnect with each other at their upstream ends so as to create a composite groove in each flat sidewall 107 and guard against possible clot formation by facilitating washing. The grooves each have central working sections defined by inboard arcuate sidewalls 115a and outboard arcuate sidewalls 115b of complementary curvature. Similarly, the arcuate ears have inboard and outboard walls 117a, 117b of complementary curvature. As best seen in FIG. 10, the upper ends of the grooves are formed with flat oblique walls 119, and the upstream ends of the ears have rounded sections 121 which abut the oblique walls when the arcuate ears reach the upstream ends of the grooves. Again, the curvature of the inboard sidewalls of the grooves is matched to the curvature of the inboard walls of the ears, and the CRP (represented by the point Z in FIG. 11) is the same for each leaflet and is located exactly in the centerline plane.

When blood is flowing normally through the valve in its open position, it flows in the downstream direction indicated by the arrow B in FIG. 10. When normal blood flow ceases and backflow begins. Frictional drag forces on the flat surfaces of the main body portions 105 of the leaflets create an upstream thrust which acts about the moment arm defined by the distance between the CRP and the outboard sidewalls 115b of the grooves. The CRP is located at the centerline substantially offset from the point of engagement between the ear and the valve body groove, e.g. a distance greater than about 25% of the radius of the passageway. This construction translates the upstream thrust of the arcuate outboard surfaces 117b of the ears generally tangentially against the concave outboard sidewalls 115b of the grooves into a substantial torque upon the leaflets causing the leaflets, which were previously oriented precisely parallel to the centerline, to immediately begin pivoting movement toward the closed position orientation.

When the leaflets reach the closed position shown in FIG. 11, their downstream arcuate edges 123 seat against the cylindrical interior surface of the valve body, and upstream mating edges 125 abut each other. Should one of the leaflets 103 reach the closed position slightly prior to the other, the rounded upstream end 121 of the ear abuts the oblique wall 119 of the groove, retaining it in this position until the other leaflet completely closes and the mating edge abutment occurs. The oblique surfaces 119 are preferably oriented at a downstream angle of not less than about 120° to the centerline plane so that possible wedging of the upstream end of the ear is positively precluded. When normal blood flow again reeves, the force of the blood against the flat inflow surfaces of the leaflet body portions causes prompt pivoting in a downstream direction, which movement continues until flat wall sections 127 near the downstream end of the ears abut against straight sidewall sections 129 provided at the downstream end of each of the grooves 113, which sidewalls 129 serve as stops that orient each leaflet precisely parallel to the centerline of the valve body passageway, as shown in FIG. 10.

Figure 13:
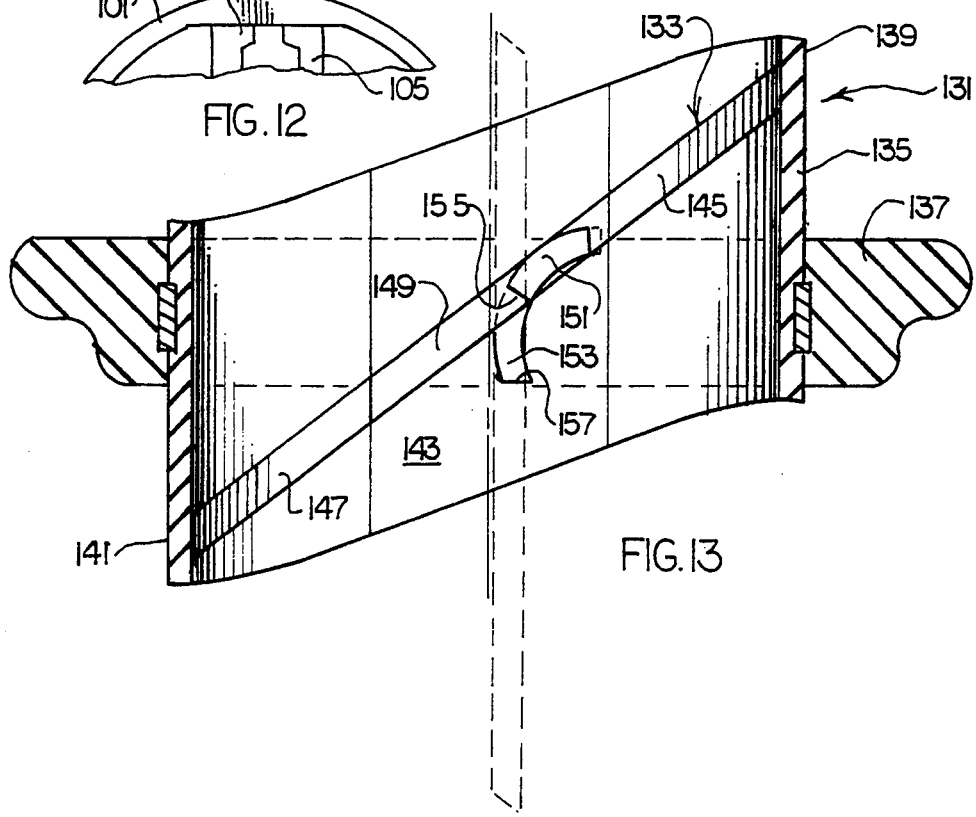
FIG. 13 is a view of still another heart valve embodying various features of the invention employing only a single occluder, which is shown in full lines in the closed position and in ghost outline in the open position.

Depicted in FIG. 13 is a heart valve 131 generally similar to that shown in FIGS. 10-12, but utilizing only a single occluder 133 in the form of a substantially flat plate of uniform thickness. More specifically, the heart valve 133 has a valve body 135 which has a right circular cylindrical exterior surface in which a groove is provided that accommodates a stiffening ring which provides support for a sewing ring 137. The valve body 135 is of generally uniform axial length but is unusually configured to have both an upstream tapered skirt 139 and a downstream tapered skirt 141, which skirts are of about equal dimension. The upstream skirt 139 extends to its greatest distance upstream of the sewing ring 137 adjacent a first or right-hand portion of the valve as illustrated in FIG. 13, and the downstream skirt 141 extends to its greatest distance downstream of the sewing ring at a second location along the left-hand portion of the valve. These first and second locations are diametrically opposed to each other and lie along a diameter which is parallel to the pair of flat sidewall sections 143 which, as explained hereinbefore, interrupt the otherwise right circular cylindrical interior of the valve body 135.

The occluder has an upstream arcuate edge surface 145, which seats against the interior surface of the valve body generally in the region of the upper skirt 139, and a downstream arcuate edge surface 147, which seats against the interior cylindrical surface of the valve body generally in the region of the downstream skirt portion 141. The occluder also has a pair of flat lateral edge surfaces 149, which lie adjacent to the flat sidewall sections 143 of the valve body. A pair of arcuate ears 151 extend outward from opposite lateral edge surfaces 149, and these ears are received in grooves 153 which are provided in the flat sidewall sections 143 of the valve body. The ears 151 have arcuate walls of complementary curvature, and the grooves 153 have similar sidewalls that are proportioned to match the curvature of the arcuate ears. The CRP is located generally near the righthand edge of the flat wall 143 so that the moment arm for closing rotation is equal to at least about 30%, and preferably between about 30 and about 40%, of the radius of the valve body passageway.

In the closed position, the arcuate upstream and downstream edge surfaces 145, 147 of the occluder 133 seat against the cylindrical interior surfaces of the valve body, and the ears 151 reside in locations slightly short of the upstream ends of the grooves 153. When the normal flow of blood resumes, the occluder rotates counterclockwise as illustrated in FIG. 13 to the ghost position shown in dot-dash lines wherein it is oriented parallel to the centerline through the valve body. Orientation in this position is achieved by the abutment of a flat end wall 155, provided at the downstream end of each ear 151, against the flat downstream end wall 157 of the grooves. In this open position, the occluder not only provides minimal resistance to blood flow through the valve body, but it nearly bisects the valve passageway and thus creates two substantially equal flow channels through the valve further minimizing pressure drop. As soon as blood flow reverses again, the drag on the flat occluder surfaces causes an upstream-directed force vector to act upon the occluder, forcing the arcuate surfaces of the ears 151 against the arcuate sidewall surfaces of the grooves 153. The engagement of such a curved surface generally tangentially against a curved surface creates the desired immediate pivoting movement.

This type of a pivot arrangement is considered to be particularly valuable for a valve with a single occluder because it permits the flat occluder, which is simple to manufacture, to be employed and to be positioned substantially at the centerline through the valve passageway, i.e. within a distance from the centerline not greater than about the thickness of the valve occluder itself. It can be very advantageous to have, in a mechanical valve, an occluder which provides minimal resistance to flow by being able to assume a precisely parallel orientation and to also divide the passageway into two channels of substantially equal cross-sectional areas. The arrangement particularly assures that both the inflow and outflow surfaces of the occluder will be well washed.

Although the invention has been described with regard to certain preferred embodiments, it should be understood that various changes and modifications as would be obvious to one having the ordinary skill in this art may be made without departing from the scope of the invention which is defined by the claims appended hereto. For example, as indicated hereinbefore, while preferred embodiments have been illustrated, these designs lend themselves to the reversal of parts, and the use of ears protruding from the occluders and grooves in the valve body sidewall can generally be replaced by rails carried by the valve body that are received in notches in the edges of the occluder. Although certain of the pivot mechanisms are illustrated with respect to only bi-leaflet valve constructions, it should likewise be understood that these are likewise adaptable for use in a single occluder heart valve. Particular features of the invention are emphasized in the claims that follow.

What is claimed is:

1. A prosthetic heart valve comprising a generally annular valve body having an interior sidewall which defines a central passageway therethrough for passage of blood in a downstream direction, said passageway being of generally circular cross-section and having a centerline extending downstream, occluder means formed by a pair of leaflets each having an inflow surface and an outflow surface, which occluder means is mounted in said valve body to alternately permit flow of blood therethrough in a downstream direction when in an open position and block flow of blood in a reverse direction when in a closed position, said valve body and said occluder means being interconnected by a pivot arrangement by which said occluder means is guided in pivoting between open and closed positions, said pivot arrangement including slidingly interengaging arcuate protrusions on one of said leaflets or said valve body and arcuate groove means in other of said leaflets and said valve body, which protrusions and arcuate groove means have arcuate surfaces of matching curvature and are such that closing movement is initiated and performed when one of said arcuate surfaces is thrust generally tangentially against said interengaging arcuate surface resulting in relative sliding movement of said protrusions in said groove means, said pivoting being about a fixed axis which is located not farther away from said centerline than a distance equal to about 3% of a radius of said central passageway.

2. A prosthetic heart valve according to claim 1 wherein said pivot arrangement includes means mounting each leaflet of said pair about a fixed axis which is collinear and is located at about the centerline through said central passageway.

3. A prosthetic heart valve according to claim 2 wherein said valve body has a pair of diametrically opposed flat sections in said interior sidewall and wherein said arcuate protrusions each have two arcuate walls which are arcs of concentric circles.

4. A prosthetic heart valve according to claim 3 wherein said groove means comprises an arcuate groove in each said flat section in said interior sidewall of said valve body and wherein said protrusions comprise an ear extending from a lateral edge of each leaflet, which ear is accommodated in one of said arcuate grooves for sliding movement therewithin, said arcuate grooves having inboard and outboard curved sidewalls and said ears having complementary inboard and outboard curved walls.

5. A prosthetic heart valve according to claim 4 wherein said leaflets have substantially flat inflow and outflow surfaces and are of substantially uniform thickness except for thickened side sections from which said ears extend.

6. A prosthetic heart valve according to claim 4 wherein said leaflets have cylindrical inflow and outflow surfaces that are each sections of a surface of a cylinder and wherein said pivot arrangement is such that said leaflet inflow and outflow surfaces assume an orientation substantially parallel to said valve centerline when in an open position.

7. A prosthetic heart valve comprising a generally annular valve body having an interior sidewall which defines a central passageway therethrough for passage of blood in a downstream direction, said passageway having an axial centerline extending downstream, said interior sidewall being generally cylindrical except for a pair of diametrically opposed flat sections which are substantially parallel to each other, occluder means having an inflow surface and an outflow surface, which occluder means is mounted in said valve body to alternately permit flow of blood therethrough in a downstream direction when in an open position and block flow of blood in a reverse direction when in a closed position, said inflow surface and said outflow surface both being rectilinear surfaces, said valve body and said occluder means being interconnected by a pivot arrangement, which includes arcuate groove means located in regions of said flat sections of said valve body and includes ear means extending from said occluder means received in said groove means, by which said occluder means is guided in pivoting between open and closed positions, said pivoting being about a fixed axis which is perpendicular to planes in which said diametrically opposed flat sections lie, said pivot arrangement being so constructed that, in said open position, said occluder means can assume an orientation wherein said rectilinear surfaces are parallel to said centerline, whereby said occluder means will reliably close as a result of where said fixed axis is located.

8. A prosthetic heart valve according to claim 7 wherein said occluder means includes a pair of leaflets and wherein said pivot arrangement for each leaflet includes an arcuate groove in each said flat section of said valve body and an ear extending from each lateral edge of each leaflet, which ear has arcuate outboard and inboard surfaces and is accommodated in one of said arcuate grooves for sliding movement therewithin.

9. A prosthetic heart valve according to claim 8 wherein said inflow and outflow surfaces are flat, and wherein each said arcuate groove has a wall in a downstream section thereof which serves as a stop by engaging said ear when said leaflet reaches an open orientation wherein said flat inflow and outflow surfaces are parallel to said centerline.

10. A prosthetic heart valve according to claim 8 wherein said pivot arrangement mounts each leaflet of said pair so that said fixed axis about which said leaflet pivots lies on or near said centerline.

11. A prosthetic heart valve according to claim 8 wherein each said leaflet has outflow and inflow surfaces, each of which surfaces is a section of a surface of a cylinder, and wherein said leaflets have downstream mating edge surfaces which seal against each other in a closed position.

12. A prosthetic heart valve according to claim 4 wherein said fixed axis about which each said leaflet pivots is perpendicular to planes in which said flat sections lie and is essentially tangent to said cylindrical outflow surface when said leaflet is in an open orientation.

13. A prosthetic heart valve according to claim 7 wherein said pivot arrangement includes an arcuate rail protruding from each said flat section of said valve body and wherein said occluder means has a pair of opposite lateral edge surfaces and an arcuate notch in each lateral edge surface thereof, which arcuate notch has facing concave and convex sidewalls of generally complementary curvature, said rails being received within said arcuate notches for sliding movement of said notches along said rails.

14. A prosthetic heart valve according to claim 7 wherein said occluder means is formed by a single valve member which completely blocks said central passageway when in a closed position.

15. A prosthetic heart valve according to claim 14 wherein said valve member has a main body section of uniform thickness with parallel flat inflow and outflow surfaces and wherein said pivot arrangement for said single valve member is such that said fixed axis is located exterior of said main body section.

16. A prosthetic heart valve according to claim 15 wherein said pivot arrangement includes an arcuate groove formed within each said flat section of said valve body, wherein said single valve member has a pair of laterally extending ears each having arcuate inboard and outboard surfaces, which ears are each received within one said arcuate groove in one of said valve body flat sections for sliding movement therewithin along complementary inboard and outboard curved sidewalls forming said groove, said arrangement being such that said valve member reaches an orientation in an open position with said flat inflow and outflow surfaces parallel to said centerline and with said valve member substantially bisecting said central passageway and creating two flow channels of substantially equal cross sectional area.

17. A prosthetic heart valve according to claim 14 wherein an annular sewing ring is attached exterior of said valve body, and wherein said valve body has an upstream tapered skirt and a downstream tapered skirt, which skirts are of about equal dimensions, said upstream skirt extending a greatest distance upstream of said sewing ring at a first location and said downstream skirt extending a greatest distance downstream of said sewing ring at a second location, said first and second locations being diametrically opposed and lying along a diameter of said valve body passageway which is parallel to said flat sections of said valve body.

18. A prosthetic heart valve comprising a generally annular valve body having an interior sidewall which defines a central passageway therethrough for passage of blood in a downstream direction, said passageway having a centerline extending downstream, said interior sidewall being generally cylindrical except for a pair of diametrically opposed flat sections, a pair of leaflets each having an inflow surface and an outflow surface, each said inflow surface and each said outflow surface being a rectilinear surface, which leaflets are mounted in said valve body to alternately permit flow of blood therethrough in a downstream direction when in an open position and block flow of blood in a reverse direction when in a closed position, said valve body and said leaflets being interconnected by an interengaging pivot arrangement located in regions of said flat sections and along lateral edges of each of said leaflets, by which arrangement said leaflets are guided in pivoting between open and closed positions, each said leaflet having a mating upstream edge, which upstream mating edges abut each other in a closed position, said pivoting of said leaflets being about fixed axes which are collinear, and said pivot arrangement being constructed so that said fixed axis is substantially offset from locations where there is interengagement between said valve body and said leaflets and so that each said leaflet assumes an open position orientation wherein said rectilinear surfaces are parallel to said centerline, whereby said leaflets reliably close upon reversal of blood flow through said valve.

19. A prosthetic heart valve according to claim 18 wherein each said leaflet has an outflow and inflow surface that is a section of a surface of a cylinder.

20. A prosthetic heart valve comprising a generally annular valve body having an interior sidewall which defines a central passageway therethrough for passage of blood in a downstream direction, said passageway having a centerline extending downstream, said interior sidewall being generally cylindrical except for a pair of diametrically opposed flat sections, a pair of leaflets each having an inflow surface and an outflow surface that is a section of a surface of a cylinder, which leaflets are mounted in said valve body to alternately permit flow of blood therethrough in a downstream direction when in an open position and block flow of blood in a reverse direction when in a closed position, said valve body and said leaflets being interconnected by an interengaging pivot arrangement located in regions of said flat sections and along lateral edges of each of said leaflets, by which arrangement said leaflets are guided in each pivoting about a fixed axis between open and closed positions which fixed axis is located essentially tangent to said outflow surface, each said leaflet having a downstream mating edge and an upstream arcuate edge, said downstream mating edges abutting each other and said arcuate edges abutting said interior sidewall in a closed position.

21. A prosthetic heart valve according to claim 20 wherein said pivot arrangement is so constructed that each said leaflet assumes an open position orientation wherein said inflow and outflow surfaces are parallel to said centerline whereby said leaflets reliably close upon reversal of blood flow through said valve.

* * * * *

UNITED STATES PATENT AND TRADEMARK OFFICE
CERTIFICATE OF CORRECTION

PATENT NO. : 5,376,111
DATED : December 27, 1994
INVENTOR(S) : Bokros, et al.

It is certified that error appears in the above-indentified patent and that said Letters Patent is hereby corrected as shown below:

Column 14, line 3 (Claim 12), change "claim 4" to --claim 11--.

Signed and Sealed this

Twenty-first Day of March, 1995

Attest:

BRUCE LEHMAN

Attesting Officer     Commissioner of Patents and Trademarks